United States Patent [19]
Anderson

[11] Patent Number: 5,880,774
[45] Date of Patent: Mar. 9, 1999

[54] NON-INVASIVE INSPECTION PLATEN

[75] Inventor: Charles H. Anderson, Dallas, Tex.

[73] Assignee: Texas Instruments Incorporated, Dallas, Tex.

[21] Appl. No.: 81,903

[22] Filed: Jun. 23, 1993

Related U.S. Application Data

[63] Continuation of Ser. No. 874,927, Apr. 28, 1992, abandoned.

[51] Int. Cl.$^6$ .......................................................... H04N 7/00
[52] U.S. Cl. ............................ 348/126; 348/131; 348/132
[58] Field of Search ..................................... 358/101, 106; 269/20, 21; 348/126, 131, 132, 125

[56] References Cited

U.S. PATENT DOCUMENTS

| | | | |
|---|---|---|---|
| 4,184,472 | 1/1980 | Benedicto et al. | 269/21 |
| 4,379,308 | 4/1983 | Kosmowski et al. | 358/101 |
| 4,648,053 | 3/1987 | Fridge | 348/126 |
| 4,672,437 | 6/1987 | Casper | 358/101 |
| 4,686,565 | 8/1987 | Ando | 358/101 |
| 4,723,766 | 2/1988 | Beeding | 269/21 |
| 4,787,800 | 11/1988 | Sone et al. | 269/21 |
| 4,872,052 | 10/1989 | Liudzius et al. | 358/107 |
| 5,056,765 | 10/1991 | Brandstater | 269/20 |
| 5,058,982 | 10/1991 | Katzir | 385/33 |
| 5,189,708 | 2/1993 | Cox | 358/101 |

*Primary Examiner*—Minsun Oh Harvey
*Attorney, Agent, or Firm*—Charles A. Brill; Frederick J. Telecky, Jr.; Richard L. Donaldson

[57] ABSTRACT

A non-invasive inspection system is disclosed. The system contains light sources or source, viewing optics, an x-y table, and a platen for mounting objects to be inspected. The transparent platen contains a vacuum system that sets up a laminar flow of air which in turn holds the objects in place without altering or damaging the devices, and allows for analysis of light transmitted through devices. The method for operating the system is also included.

14 Claims, 4 Drawing Sheets

NON-INVASIVE INSPECTION PLATEN

This application is a continuation of application Ser. No. 07/874,927 filed Apr. 28, 1992, which is now abandoned.

BACKGROUND OF THE INVENTION

1. Field of the Invention

This invention relates to inspection platens, more particularly to inspection platens that do not require an alteration of the material to be inspected.

2. Background of the Invention

Inspection for defects is critical in any process of manufacture. Whether the inspection is used as an end process or used in setting up the manufacturing flow, it is important that the inspection system be exact and thorough. Recently, companies have begun to move to automated inspection systems to eliminate both the overhead of a huge inspection effort and to provide more consistent results.

Inspection systems typically have some kind of viewing apparatus with a platform or platen to which is mounted the object of interest. The object is often held through vias in the object or device with a vacuum from under the platen or in some type of carrier. These have many problems, two of which are the vias themselves, and the uniformity of the objects surface.

The vias are normally cut into the carrier, platform or platen some small distance from the edge. This has obvious problems when inspecting thin films, where the vias may propagate into cracks if in the object, or cause other defects of visible anomalies if milled into a platen. Additionally, if the object of interest is a thicker item, such as an integrated circuit, the carrier may not hold the IC down enough to flatten any "potato chipped" areas of the chip uniformly, which can lead to problems in the inspection accuracy.

Another problem the current systems possess is in the inspection of translucent or transparent materials, from white ceramic to fiber optic cables. In these cases the platen must be glass or some similarly transparent material, and the vias would cause problems in the final product, since the light would be transmitted differently through the holes or vias than through other parts of the system. Therefore, some type of non-invasive means of holding objects to a platen that does not invade the material and allows the passage of light is needed.

SUMMARY OF THE INVENTION

The present invention disclosed herein comprises a non-invasive inspection system that allows objects to be inspected without alteration. The system has a transparent platen onto which is mounted a vacuum manifold system. The vacuum manifolds are situated so as to cause a laminar flow of air over any object put between two or more of them and against the glass. The flow of air forces the object down onto the glass, making it uniformly flat, providing more consistent inspections. Additionally, the system has the capability of inspecting transparent materials, such as fiber optic cables, and using varied wavelengths and structures of light to inspect a wide variety of objects.

BRIEF DESCRIPTION OF THE DRAWINGS

For a more complete understanding of the present invention and for further advantages thereof, reference is now made to the following Detailed Description taken in conjunction with the accompanying Drawings in which.

DETAILED DESCRIPTION OF THE PREFERRED EMBODIMENTS

Figure 1:
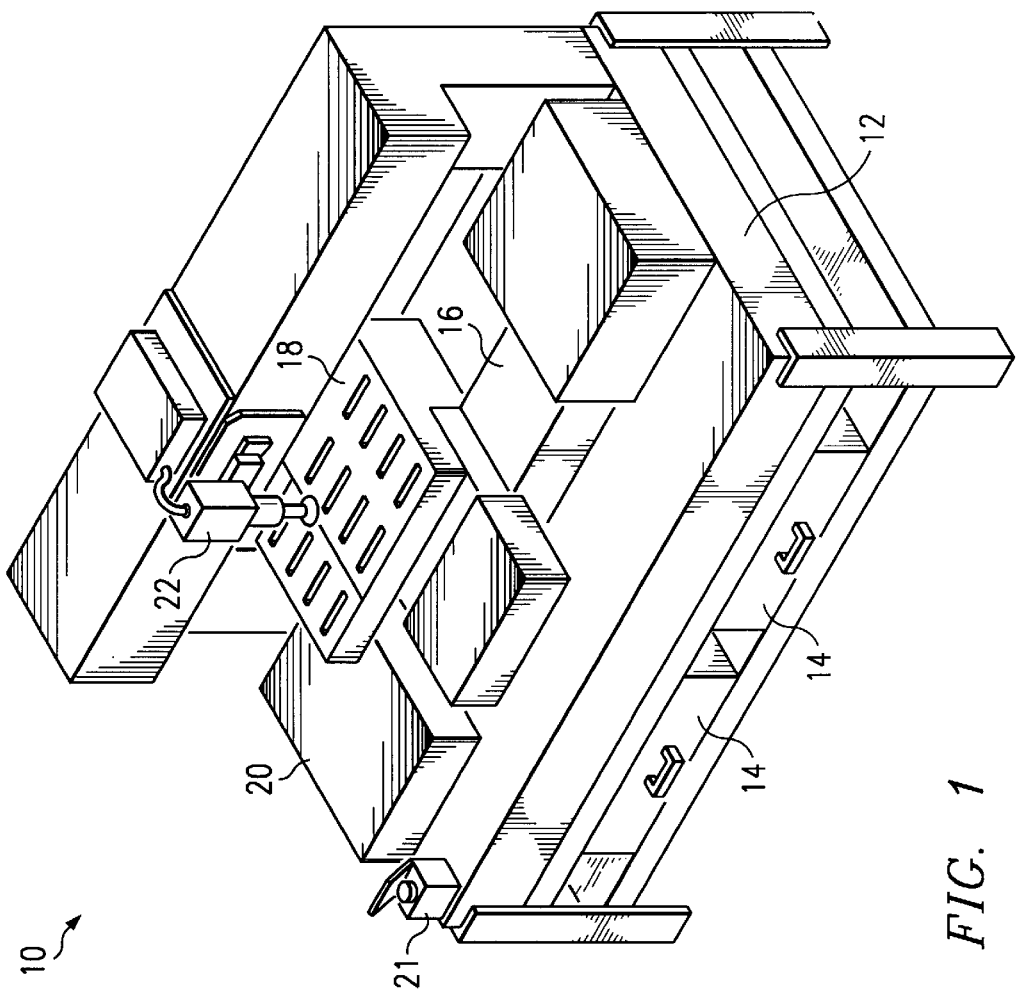
FIG. 1 shows an inspection system.
Figure 1:
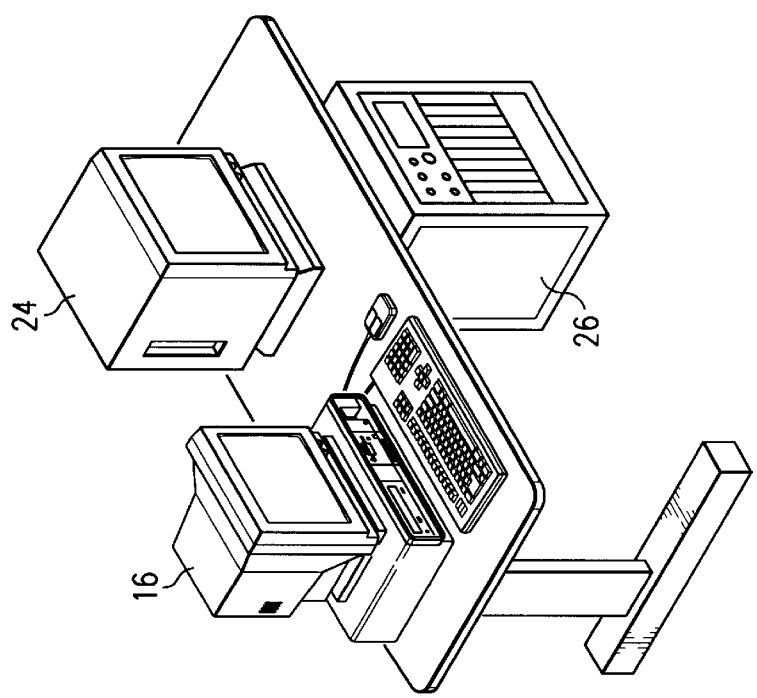

FIG. 1 shows an inspection system 10 used to inspect a variety of different objects. The system is mounted on a large table or platform 12 made of a heavy material such as granite for stability. The drive electronics and interface electronics for the application shown reside inside the table and are accessed by drawers 14. A mobile mounting structure such as an x-y inspection table 16 allows the vision system camera and optics 22 to view the entire set of objects without operator intervention. The objects under inspection receive illumination from a strobed transmission light system 18 below the platen 20. On the platen 20 are the devices under inspection. Module 22 normally contains a camera and optics, plus a second strobed illumination source for top-side illumination.

The camera used depends upon the system requirements, but an, example might be a 1000×1000 pixel charge-coupled device (CCD) camera. The camera feeds information into a machine vision system 28, such as a multi-processor gray-scale system for parallel high-speed processing. A monitor 24 is typically connected to this system for viewing. A color monitor may be used for feature highlighting. A digital monitor menu-driven statistics display 26 often accompanies the inspection system for analysis of data from the vision system. Additionally, the system may contain an emergency stop button 21 which shuts down the system in case of malfunction. The above system minimizes user interface to the physical components since it is a totally automated inspection system. Additionally, a unique vacuum platen 20 that assists in minimizing error is used with the above system.

Figure 2:
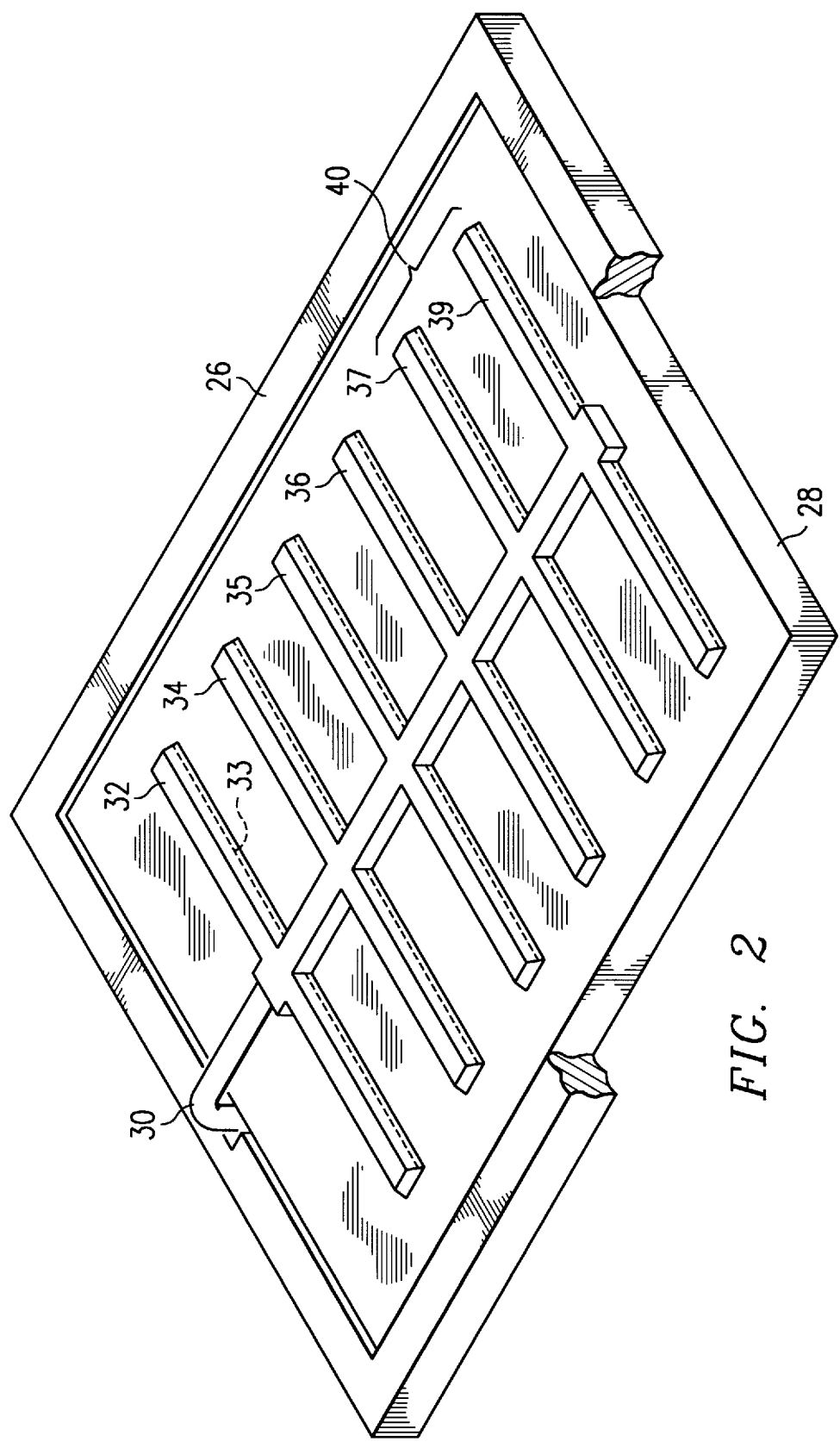
FIG. 2 shows a perspective view of a non-invasive inspection platen, with the vacuum off-platen.

In FIG. 2, the platen with the vacuum structure is shown. The vacuum connects to the structure via passage 30. The vacuum pulls air in through the individual ports 33, which are on both sides of rails 34, 35, 36, and 37. Rails 32 and 39 have ports on one side only. The devices rest in the spaces 40 against the glass platen 28. The glass platen is mounted on a metal frame 26 for mating to the x-y table of the inspection system of FIG. 1.

The positioning of the devices between two rails causes the air flow to be laminar in manner. The flow of the air holds the device edges down, and pulls it flat against the platen. This is especially important if there are any surface irregularities on the side of the device to be inspected that is against the glass. The air flow pulls the device flat, eliminating any "potato chipping" and allowing for more uniform inspection.

Figure 3:
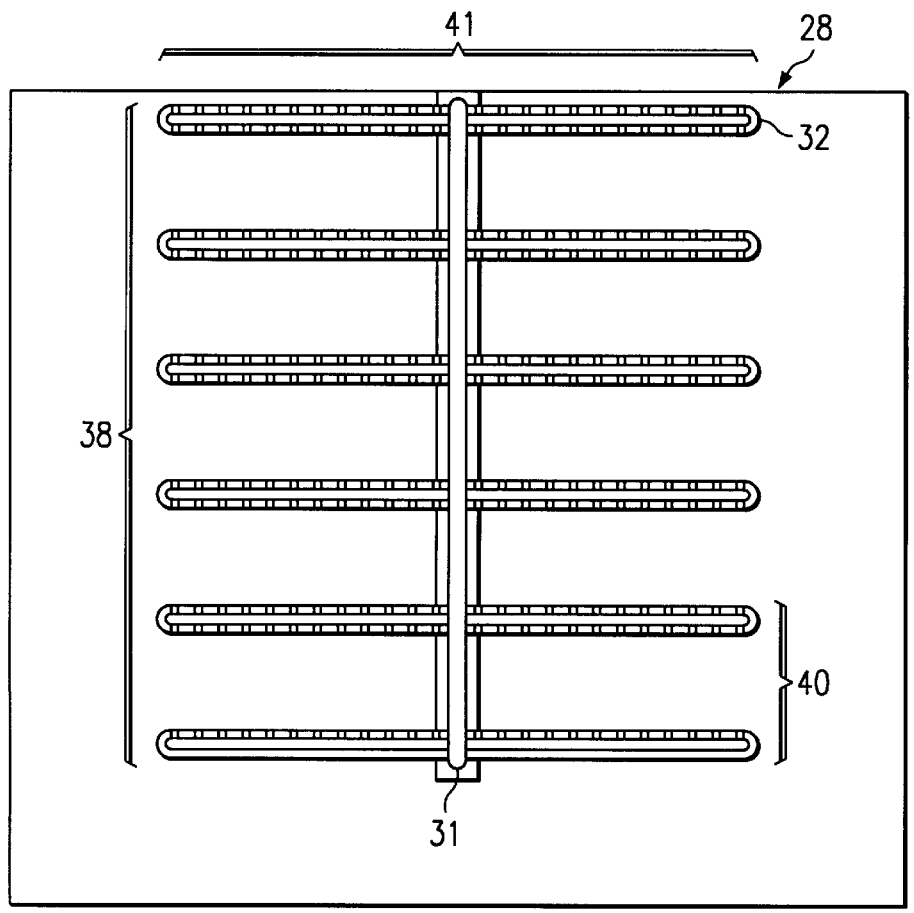
FIG. 3 shows a top view of a non-invasive inspection platen.

FIG. 3 shows the underside of the glass platen 28 with the vacuum rails mounted on the other side of the glass from the viewer. Ideally, all dimensions could be manipulated. The length of the rails 40 can be changed by telescoping the rails so they could be made longer if needed. The main vacuum channel 31 could also be telescoped to extend its length. Additionally, the distance 41 should be able to change with the size of the objects to be inspected, to allow more flexibility in the platens.

The flexibility and adaptability desired could be accomplished in many ways. One way is to cement the manifolds onto the glass and have many manifolds for many different ranges of sizes. This method is costly, but may result in better accuracy and a tighter vacuum seal of the devices to the glass when the vacuum is operated. Other methods of mountings are available. Possibly, the rails and main channel could have a rubberized pad underneath them that will adhere to glass on contact by pressure or suction. It is also possible to cause things to stick to glass with static, but this may cause problems with the objects under inspection if they are active devices.

Figure 4:
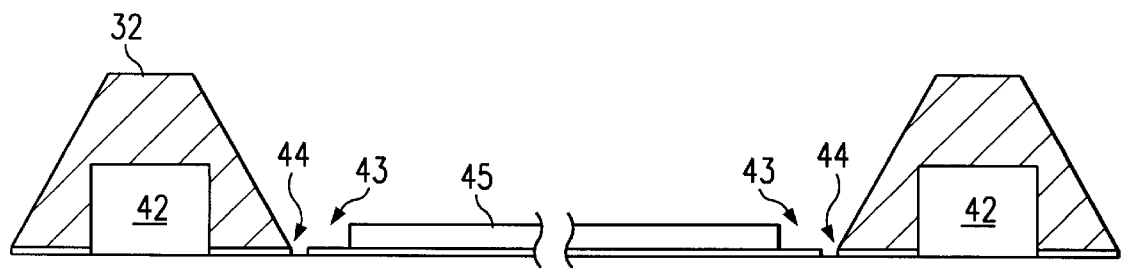
FIG. 4 shows a cross-sectional view of one region of a non-invasive inspection platen.

FIG. 4 shows a cross section of a pair of vacuum rails. The air flow travels from the room in the directions of arrows 43, into the rails via the very small ports 44. The ports 44 lead into the rail channels 42 and down into the main channel 31 from FIG. 2. The device 45 would be set into the space between the rails and the air flow would apply force to the edges of the device, pulling slightly inward towards the rails. This causes the device to lie flat against the glass. If the objects under inspection are fiber optic materials, spatial light modulators or some other object where the light is being transmitted through the object or even reflected off of the object, some type of anti-reflective coating should be applied to the platen. This will offer an even better view of the objects in question.

Figure 5:
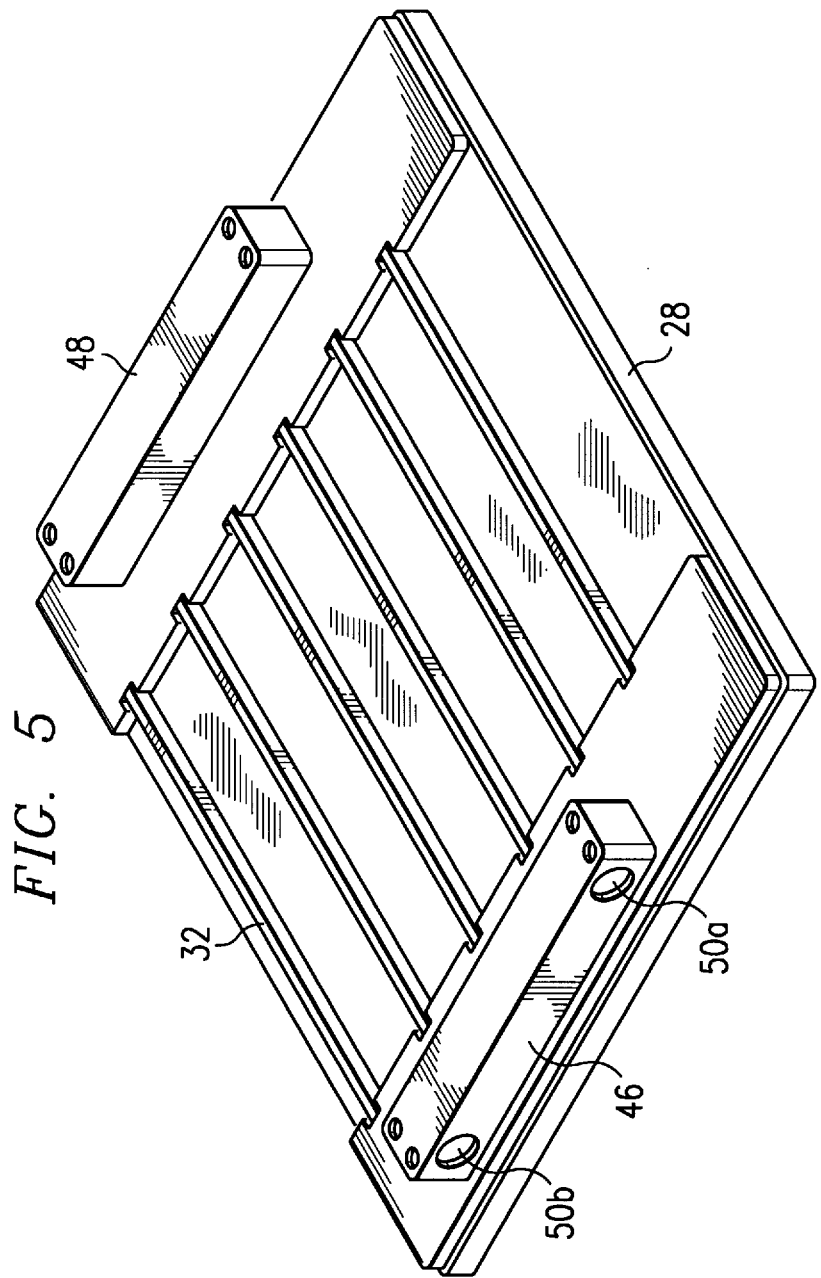
FIG. 5 shows a platen with the vacuum ports on-platen.

For objects that require more force or a more rigid rail structure, the vacuum is mounted on a side platform of the platen, shown in FIG. 5. This eliminates the distance between the vacuum and the ports that was in the embodiment of FIG. 2. Additionally, the rails in this embodiment are fixed, which may be an advantage if the devices require a higher amount of pressure from the vacuum. The port inlet blocks 46 and 48 are mounted directly onto the glass platen. The vacuum is connected directly to the ports 50a and 50b on block 46, which are repeated on block 48.

The above embodiments offer advantages over the currently available inspection systems. This system in all of its embodiments allows for a wide range of devices to be inspected, from thin films to fiber optic cables. It also provides a uniformity of surface and a transparent platen for automated microscopic viewing of many materials that were only visually inspected previously. Further it accomplishes the inspection with no damage or alteration of the objects to be inspected.

Thus, although there has been described to this point particular embodiments of a non-invasive inspection system, it is not intended that such specific references be considered as limitations upon the scope of this invention except in-so-far as set forth in the following claims.

What is claimed is:

1. An automated inspection system comprising:
  a. a stable platform;
  b. a mounting structure connected to said platform to allow objects to be inspected;
  c. a vacuum platen with manifolds that cause a laminar flow of air to hold said objects in place on said platen, wherein said platen has contact with said mounting structure to allow movement of said platen which holds said objects;
  d. at least two illumination sources to allow illumination of said objects to be inspected, wherein at least one of said sources allows top-side illumination and at least one of said sources allows for illumination from below said objects;
  e. a camera for viewing said objects to be inspected, wherein said camera is arranged such that it may receive light from any of said sources;
  f. a vision system for converting information from said camera to a display of what said camera is viewing; and
  g. a display device wherein said display device receives image data from said vision system.

2. The system of claim 1 wherein said stable platform contains drive electronics and interface electronics which are accessible to an operator.

3. The system of claim 1 wherein said mounting structure comprises an x-y table.

4. The system of claim 1 wherein said mounting structure comprises a mobile x-y table.

5. The system of claim 1 wherein said camera comprises a 1000×1000 pixel CCD camera.

6. The system claim 1 wherein said illumination source is below said vacuum platen.

7. The system of claim 1 wherein said illumination source is below said vacuum platen.

8. The system claim 1 wherein said system includes a statistical analysis computer.

9. A vacuum platen comprising:
  a. a flat piece of material;
  b. a series of vacuum manifold rails on said material, wherein said rails are spaced apart to allow objects to be placed between them against the material, such that no part of said object is obscured;
  c. a vacuum connected to said rails such that when said vacuum is on, the rails set up a laminar flow of air across the top of said objects and cause said objects to adhere to said material in a substantially flat manner.

10. The platen of claim 9 wherein said flat piece of material is glass.

11. The platen of claim 9 wherein said vacuum manifold rails are fixed in place.

12. The platen of claim 9 wherein said vacuum manifold rails are movable.

13. The platen of claim 9 wherein said vacuum mounted on said piece of material.

14. The platen of claim 9 wherein said vacuum is attached to said vacuum manifold rails without being mounted said flat piece of material.

* * * * *